United States Patent [19]

Cahill et al.

[11] Patent Number: 5,564,487

[45] Date of Patent: Oct. 15, 1996

[54] CONTINUOUS CASTING MOLD HAVING RADIATION SOURCE FOR LEVEL MEASUREMENT

[75] Inventors: Bonaventure B. Cahill, Edgewood, Ky.; Jack H. Adkins, Milford, Ohio

[73] Assignee: Ronan Engineering Company, Florence, Ky.

[21] Appl. No.: 170,047

[22] Filed: Dec. 17, 1993

[51] Int. Cl.⁶ .......................... B22D 11/04; B22D 11/18; B22D 11/20
[52] U.S. Cl. .................... 164/151.3; 164/413; 164/450.2
[58] Field of Search .......................... 164/151.3, 154.5, 164/450.2, 413, 451, 453, 454

[56] References Cited

U.S. PATENT DOCUMENTS

| | | | |
|---|---|---|---|
| 4,735,253 | 4/1988 | Vaterlaus | 164/450.2 X |
| 4,739,819 | 4/1988 | Eriksson et al. | 164/151.3 |
| 5,072,774 | 12/1991 | Schilcher | 164/450.2 X |

FOREIGN PATENT DOCUMENTS

| | | | |
|---|---|---|---|
| 0153918 | 9/1985 | European Pat. Off. | |
| 1508806 | 11/1969 | Germany | 164/450.2 |
| 58-205666 | 11/1983 | Japan | 164/450.2 |
| 286828 | 12/1977 | U.S.S.R. | 164/405.2 |

Primary Examiner—J. Reed Batten, Jr.
Attorney, Agent, or Firm—Kinney & Schenk

[57] ABSTRACT

A continuous casting mold comprises a mold tube encased in a water jacket. A radioactive source on one side of the mold tube and scintillation crystal detector on the opposite side of the mold tube are employed to gauge the level of the molten metal in the tube. The amount of radioactive source material is maintained at an inherently safe level by disposing the source material in one or more recesses in the wall of the mold tube and by employment of a "gel" light tube connection between the scintillation crystal and a photomultiplier.

24 Claims, 14 Drawing Sheets

CONTINUOUS CASTING MOLD HAVING RADIATION SOURCE FOR LEVEL MEASUREMENT

The present invention relates to improvements in gauging various conditions as a function of the amount of radiation absorbed and more particularly to improvements in gauging the level of molten metal during the continuous casting of billets, blooms, slabs and the like.

Radiation absorption gauging, in its basic terms, comprises the provision of a radioactive source and a detector spaced therefrom. The radioactive source is a material that is continuously disintegrating material which emits particles/energy in the form of alpha, beta and gamma rays in transmiting to a lighter, elemental material. The detector is responsive to the impingement of these particles/energy to provide a given signal level, which is inversely proportionate to the square of the distance between the source and detector.

When an object is disposed between the source and the detector, or the aggregate density of the medium between the source and the detector is otherwise increased, the source emissions will be absorbed by the increased mass of the intervening medium and the output signal from the detector will be proportionately reduced.

This principle, for example, can be used to detect the amount of sand on a belt conveyor by disposing a source below (or above) the conveyor and a detector above (or below) the conveyor. The source and/or the detector are transversely elongated so that the radiation field impinging on the detector passes through the full width of the sand that is deposited on the traveling belt. The density of the sand is proportionate to its volume. Thus, when the correct volume of sand is on the belt, the detector will have a given magnitude. If the volume of sand varies from the desired volume, the variation will be reflected by a variation in the detector output signal.

The same principle is involved in gauging the level of molten metal as it is poured into a mold in a continuous casting process. In this process, the mold comprises a vertically disposed, water jacketed tube into which the molten metal is poured. The molten metal is chilled to a solid form and drawn from the lower end of the tube as a part of the continuous casting process. In order to properly control this continuous casting process it is necessary to gauge the level of molten metal in the tube to thereby provide a signal for controlling the rate at which metal is poured into the tube and/or the chilled metal is withdrawn from the tube.

In gauging the level of molten metal, the radioactive source is disposed either outside the metal jacket or in the cooling water chamber of the water jacket, on one side of the mold tube. The detector is similarly disposed, on the opposite side of the mold tube, outside the water jacket or in the cooling water chamber of the water jacket. There is thus created a radiation field that spans a portion of the height of the mold tube adjacent its upper end. The intensity of the radiation impinging on the detector, and the output signal therefrom, is inversely proportional to the degree to which molten metal absorbs radiation, which in turn is a function of the level of the molten metal in the tube.

The described examples of radiation gauging have in common the fact that there is an environmental, fixed, radiation absorber, in addition to the physical item to be monitored by radiation absorption. In the first case, the fixed absorber is the conveyor belt. In the case of gauging the level of molten metal, the fixed absorber comprises the walls of the mold tube, two steel plates that define a cooling water flow path and several layers of water, and, in many cases, the steel outer walls of the water jacket.

The point being made is that the fixed absorbers set a threshold value of radiation strength that must be exceeded in order to be able to measure the condition of interest, i.e., the amount of sand on the belt or the level of metal in the mold tube.

While not necessarily so limited, the present invention focuses on the radioactive absorption gauging of the level of molten metal in a mold tube in a continuous casting process.

While there are literally hundreds of man made radioactive materials in the form of isotopes, as well as many naturally occurring radioactive materials, man made, cesium-137 has been found uniquely suited as the radioactive source material for absorption gauging and particularly in gauging the level of molten metal in a continuous casting process. There is a second radioactive material that can be advantageously employed in radiation gauging, and in molten level gauging in particular, namely cobalt-60, also a man made isotope. This isotope has a higher energy level, which reduces the amount of material required (as measured by millicuries). However cobalt-60 has a shorter half life than cesium-137 (5.5 years v. 30 years) and for that reason cesium-137 is preferred.

In any event, the fixed absorbers in molten metal, level gauging have led to the use of radioactive sources of relatively large amounts.

At this point it needs to be recognized that not all radioactive material necessarily involves an undue health or environmental hazard. This is to point out that there is continual background radioactivity in all parts of the world. This is a very low level of radioactivity, but nonetheless it exists and is measureable. It also may vary from one locale to another.

For purposes of the present invention, radioactive material in amounts that have a strength generally in the same order of magnitude as background radiation are deemed inherently safe in that they does not pose any significant health risk or environmental hazard.

Gamma ray emitting isotopes, such as cesium-137 and cobalt-60 in small amounts are essentially safe. Specifically cesium-137 in units of less than 10 micro-curies and cobalt-60 in units of less than 1 micro-curie, are quantities of radioactive material that fall within the definition of what is deemed inherently safe. The safety of these small units of radioactive material is enhanced by their being encapsulated in steel, or similar, rugged material, such as monel. It is further preferred that these exempt units be marked to identify the isotope that is encapsulated. It has also been determined that up to ten of these inherently safe, radioactive units may be combined into a single device without creating a health or environmental hazard.

Commercial acceptance of radiation gauging in general and molten metal level gauging in particular has been limited by the perceived need to employ radioactive sources which comprise quantities that have a strength in excess of what would be an inherently safe amount. Again, with particular reference to molten metal level gauging, the conventional radioactive sources have employed quantities of cesium-137 substantially in excess of 10 micro-curies and quantities of cobalt-60 substantially in excess of 1 micro-curie.

The relatively large amounts of radioactive material are inherently expensive and, for that reason alone, are a deterrent to the use of radiation gauging.

More importantly, use of units of radioactive material in excess of inherently safe strengths invokes a plethora of governmental regulation.

For example, as a minimum, a steel mill employing a radiation gauging process would need a governmental license (requiring the payment of an initial application fee and annual renewal fees) just to have the necessary radioactive source material on its premises. The process would have to be conducted in an area of restricted access. A named employee would have to be designated to be accountable, on behalf of the steel mill, for the location of each and every item of radioactive material that is received and for the proper storage and/or disposal of each such item. The premises of the steel mill would also be subject to both scheduled and unscheduled inspections to monitor for compliance with regulations pertaining to the use of radioactive material. There is also the burden of monetary penalties for non-compliance with applicable regulations, even where the non-compliance is unintentional. All of this is both time consuming and expensive.

Further, there is an additional governmental involvement in that shipping of radioactive units having a strength in excess of inherently safe levels, involves the transportation of a "hazardous" material and brings into play another set of governmental regulations relating to the transportation of hazardous material. Thus there is a substantial, additional transportation expense in bring radioactive material into the steel mill (or other user) as well as in shipping the radioactive material to an appropriate disposal site, after it has served its function in the gauging process.

Accordingly, one of the primary objects of the present invention is to reduce the strength of radioactive material required to perform a gauging function.

Another object of the present invention is to enable the use of inherently safe strengths of radioactive material in providing a gauging function where the gauging environment includes fixed absorbers that absorb a high percentage of the radiation field, compared to the radiation absorbed by the medium to be measured.

Another object of the present invention is to avoid the added expense of complying with governmental regulations that are applicable to the use of radioactive materials that have a strength in excess of what is deemed to be inherently safe.

In accordance with one aspect of the invention, the foregoing ends are attained through disposition of the radioactive source ha one or more recesses formed in the wall of the mold tube. By so disposing the radioactive source, the mass of the "fixed absorber" is reduced, thereby minimizing the required strength of the radioactive source.

In accordance with another aspect of the invention, the foregoing ends are attained through the provision of a "gel" light pipe connection between a scintillation crystal and a photomultiplier tube. By so doing the size of the crystal may be increased to obtain a significant increase in the sensitivity of the detector and thereby reduce the strength of the radioactive source.

In accordance with a further aspect of the invention, the foregoing ends may be attained by disposing the detector in the water bath that is employed in cooling the mold tube, to thereby decrease the distance between the detector and the radioactive source, as well as to decrease the "fixed absorber". Further, such disposition can be done in a manner that provides ready accessibility to the detector for maintenance and repair.

In accordance with broader aspects of the invention, the radioactive source comprises no more than ten source units, with each source unit being inherently safe. Preferably this end is attained through the use of cesium-137 having a strength not exceeding 10 microcuries or cobalt-60 having a strength not exceeding 1 microcurie.

In accordance with yet another broad aspect of the invention, the foregoing ends may be attained by a method in which a gauging function is performed. Such function is performed where there is a "fixed absorber" between the detector and the radioactive source, which establishes the minimum strength requirement for the radioactive source. The method is characterized by employing a given quantity of radioactive material which is inherently strength, while at the same time its strength is sufficiently high to produce a relatively low background noise to signal ratio.

The above and other related objects and features of the invention will be apparent from a reading of the following description of preferred embodiments of the invention, with reference to the accompanying drawings and the novelty thereof pointed out in the appended claims.

IN THE DRAWINGS

Figure 1:
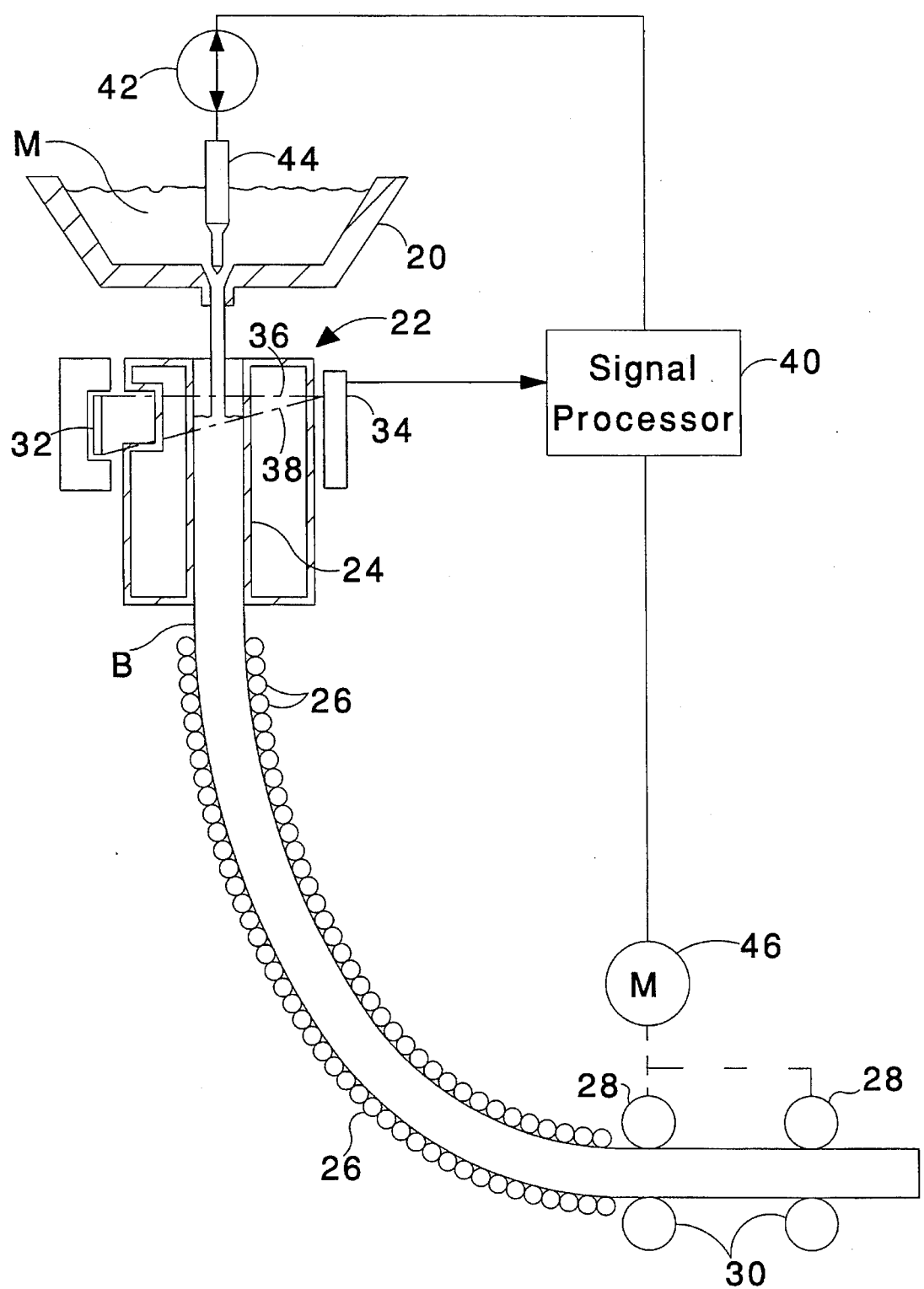
FIG. 1 is a schematic illustration of the basic components of continuous casting process in which the level gauging means of the present invention is incorporated.

FIG. 1 illustrates the basic elements of a continuous casting process in which the present invention is to be utilized. A supply of molten metal M is maintained in a container 20, that has a bottom outlet, from which the metal flows into a mold 22. The mold 22 comprises a water cooled tube 24, that chills and solidifies the molten metal so that it exits the lower end of the mold as a solid bar. The bar B follows a curved path, defined by a plurality of rollers 26, to powered feed rolls 28 which coact with idler rolls 30 to continuously feed the solidified bar B. Means downstream of the rolls 28, 30 separate lengths of the bar B for further processing.

A radiation source 32 is provided on one side of the mold 22 and a detector 34 is disposed on the opposite side the mold 22. The source 32 is a "line" type source in which radiation is emitted, in all directions along its vertical height. The detector is of the "point" type, having a radiation responsive surface of limited area. The lines 36, 38 define the bounds of radiation field emitted from the source 32 and detected by the detector 34. It will be seen the upper level of metal in the tube 24 is within the bounds of the lines 36, 38.

The detector 34 generates a gauging signal that is inversely proportional to the extent to which the metal in tube 24 blocks (absorbs), radiation that would otherwise impinge on the detector 34. There is thus provided a gauging signal that is proportional to the height of the metal in the tube 24. This gauging signal is fed to a signal processor 40. The signal processor 40 then generates a signal input to a means 42 for raising or lowering a plug 44 to thereby control the rate at which molten metal flows into the mold 22.

In this fashion, the upper level of molten metal in the tube 24 can be controlled and maintained at a given level. Alternatively, or additionally, the level of molten metal can be controlled by varying the rate at which the bar B is withdrawn from the mold 22. To this end, the rollers 28 are driven by a variable speed motor 46, having a signal input connection from the signal processor 40. If, for example, the level of metal is higher than desired, the plug 44 can be lowered to reduce the rate of molten metal flow and/or the speed of the motor 46 can be increased.

Figure 2:
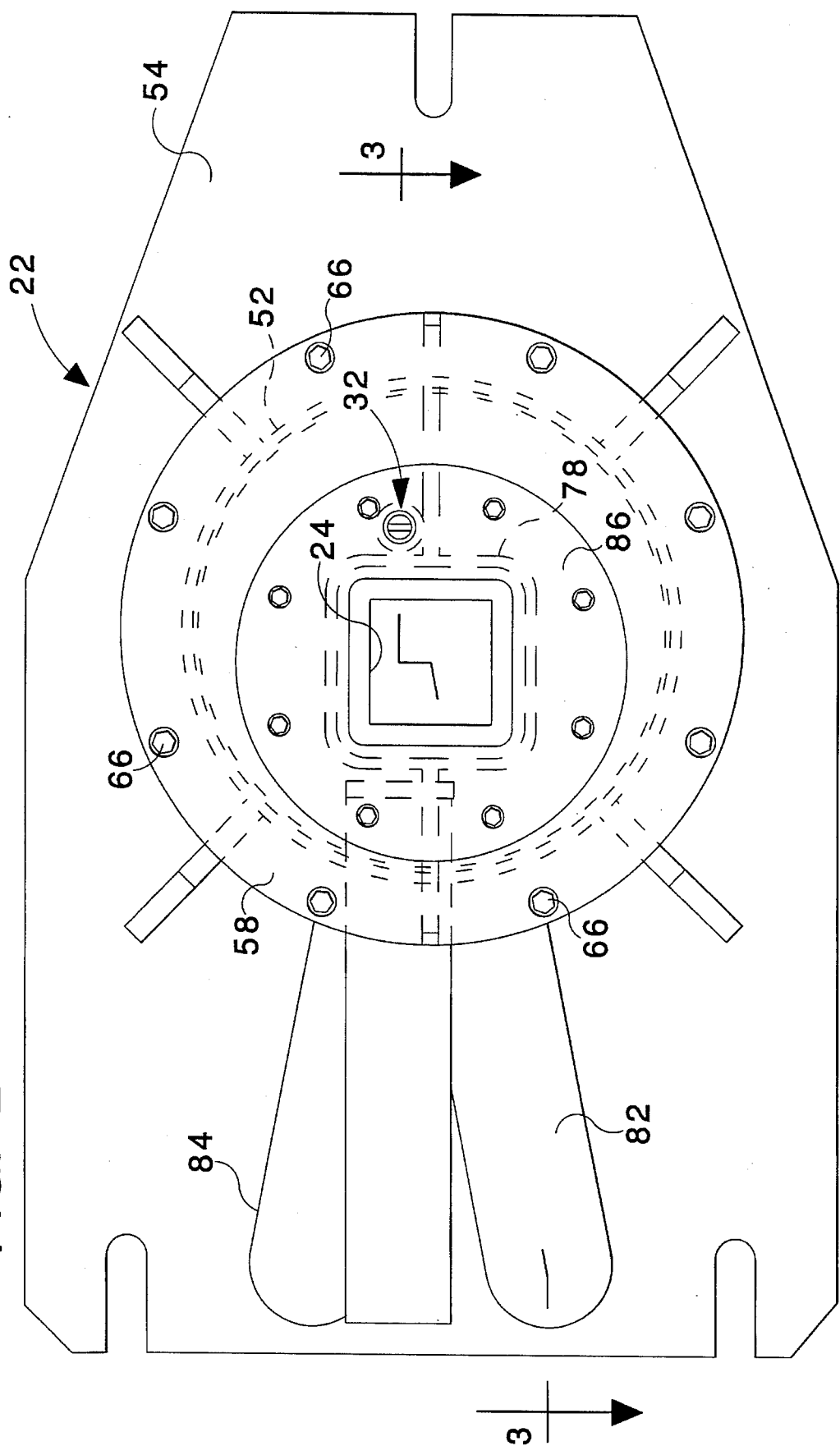
FIG. 2 is a plan view of a continuous casting mold, schematically depicted in FIG. 1.
Figure 3:
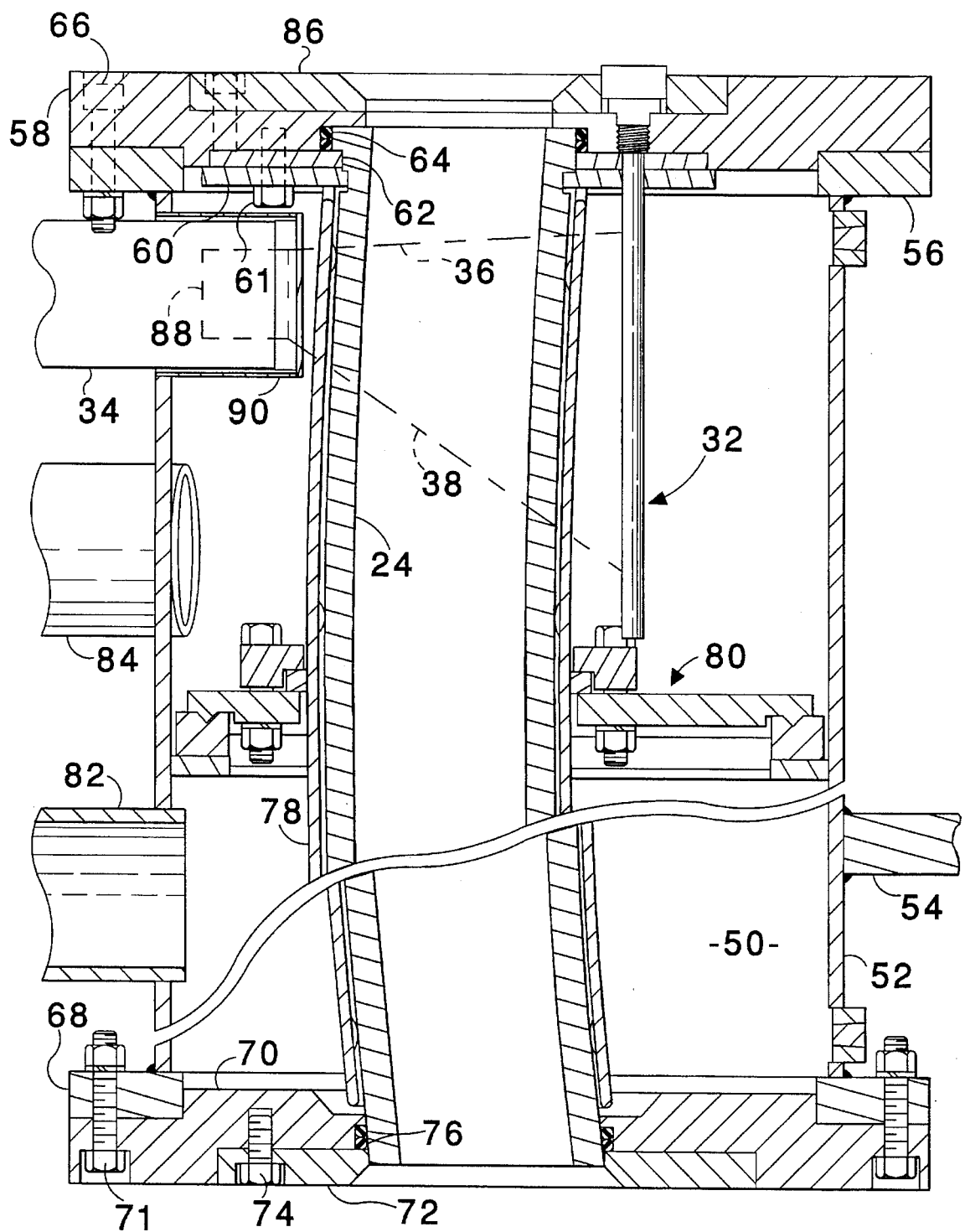
FIG. 3 is a section, on an enlarged scale, taken generally on line 3—3 in FIG. 2.

Reference is next made to FIGS. 2 and 3 for a more detailed description of the mold 22, which is of conventional design. The tube 24 defines the inner bounds of a water chamber 50, the outer bounds of which are defined by a cylindrical, water jacket tube 52. The water jacket is welded into a support plate 54 that is mounted on appropriate supports with the tube 24 appropriately aligned with the outlet of a molten metal container 20.

A collar 56 is secured to the upper end of the water jacket 52. The upper end of the mold tube 24 is secured to a mounting disc 58 by retaining plates 60, which are secured to the undersurface of disc 58 by screws 61 (one is shown). The retaining plates 60 also hold a collar 62 and sealing rings 64 in place. The latter provide a sealed connection between the tube 24 and the mounting collar 64, at the upper end of the water jacket. The mounting disc 58 is secured to the water jacket collar 56 by bolts 66. A collar 68 is secured to the lower end of the water jacket tube 52. The lower end of the tube 24 is positioned by a plate 70 that is secured to the collar 68 by screws 71. A further collar 72 is secured to the undersurface, of the plate 70 by screws 74, to clamp sealing rings 76 and provide a seal between the lower end of the water jacket and the tube 24.

The viability of a continuous casting process is first dependent on the use of a mold tube formed of copper, essentially in an unalloyed form. Since the melting point of copper is roughly 1,100° C. and molten metals, such as ferrous alloys, have melting points in excess of 1,500° C., it is essential that tube be cooled.

Not only is water cooling essential, it is further necessary to provide means for enhancing the rate of heat transfer from the tube to the water. To this end a flow defining tube 78 is mounted in closely spaced relation to the mold tube 24. The water chamber 50 is divided into upper and lower portions by interacting rings and collars indicated at 80. A tube 82 is connected to an appropriate source of pressurized, cooling water and opens into the lower portion of the chamber 50. Cooling water then flows upwardly through the narrow, surrounding passage defined by the tubes 24, 78, at a relatively rapid rate, into the upper portion the chamber 24. The cooling water is then discharged from the mold 22 by way of a tube 84.

The mold construction as shown in FIGS. 2 and 3 is typical of present continuous casting technology and has been described in detail to provide an understanding of the harsh operating environment for a gauging function, namely determining the level of molten metal in a mold tube 24.

Radiation absorption technology has long been recognized as an effective means for providing this gauging function. FIGS. 2 and 3 also illustrate one form that radiation absorption technology has taken in providing the level gauging function.

Thus, the radiation "line" source 32 is mounted in a ring plate 86, and extends through the collar 62 and one of the plates 60, into the upper portion of the water chamber 50. The detector 34 is usually in the form of a tubular member that includes a scintillation crystal 88. The water jacket tube 52 is provided with a closed end tube 90, which projects into the upper portion of the water chamber 50. The detector is mounted with the crystal at the innermost end of the closed tube 90, thereby minimizing the distance between the detector crystal 88 and the radiation emitting source 32.

FIG. 3 better illustrates the radiation field emitted by the source 32 and sensed by the crystal 88 of the detector 34. The upper bound of this radiation field is again indicated by reference character 36 and the lower bound by reference character 38.

Figure 5:
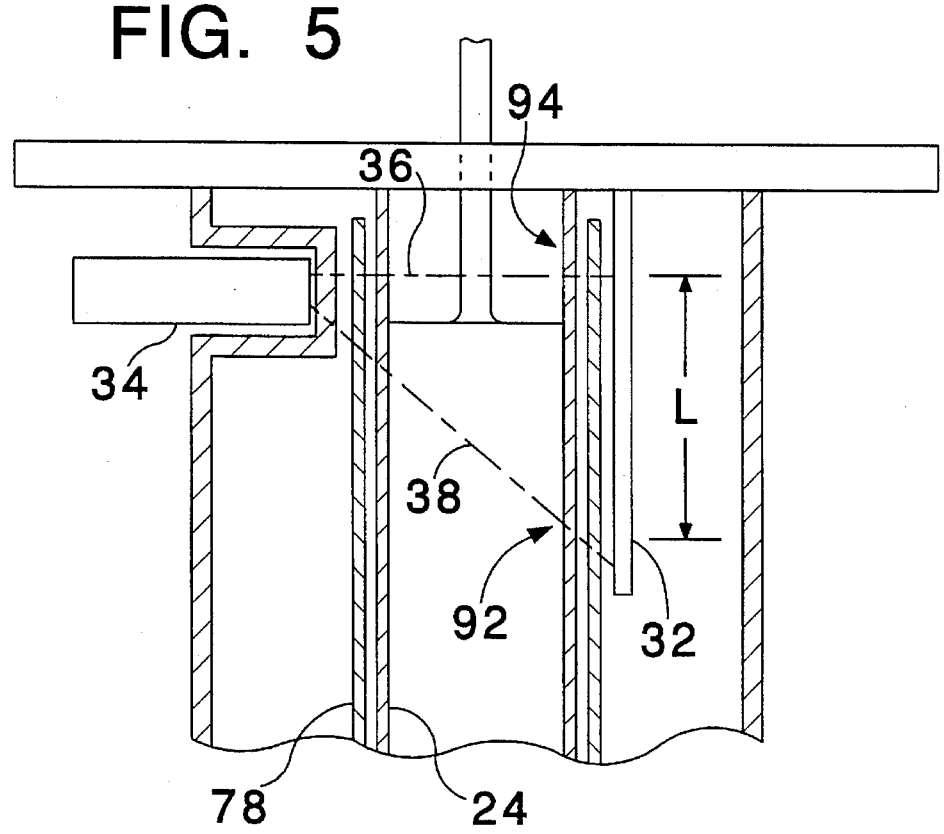
FIG. 5 is a simplified elevation of the radioactive source and detector, as shown in FIG. 4.

The source 32 has radioactive material dispersed along its height between the bounds 36, 38. The crystal 88 has a relatively small diameter and, therefore, is of relatively small lateral extent in relation to the source 32, hence its being referenced as a point detector. It will be seen that the lower bound 38 intersects the lowest level in the tube 24 at 92 and the upper bound intersects the highest level in the tube at 94. The vertical distance L, between points 92, 94 is the measuring range for the illustrated source 32 and detector 34 (FIG. 5).

At this point there will be a digression to discuss the basic principles of radiation absorption gauging technology, to provide a better understanding of the present invention.

A radioactive source is a material that is continuously disintegrating material that emits particles/energy in the form of alpha, beta and gamma rays in transmuting to a lighter, elemental material.

Radioactive materials are both natural and man made.

Radioactive materials give off particles that are distributed completely randomly, both as to direction and time.

Radiation from gamma ray (photon energy) emitting radioactive material comes as a succession of radiant energy that continues in a given direction, with undiminished energy, until deflected or absorbed.

The average intensity of radiation from an unshielded source is proportional to the source strength S (millicuries (1/1000 of the amount of radioactive material that decays at the rate of $3.7 \times 10^{10}$ disintegrations per second)). Intensity of radiation decreases as the square of the distance from the source.

$$I = \frac{KS}{d^2}$$

The constant K is available units providing an intensity measurement (I) in milli-Roentgens/hr. or in terms of flux density of the particles per second per square inch of arc perpendicular to the flux.

If an object is disposed between the radioactive source and the detector, the detector is shielded by the extent to which the radiation must pass through the object in reaching the detector. This is to say that some, if not all, of the radiation impinging on the object is absorbed by the object and does not reach the detector.

The reduction in radiation (r) is basically expressed as:

$$r = e^{\mu t}$$

Where e=natural logarithm base (2.7183); μ=the linear absorption coefficient for a given material and a given radiation source; and t=the thickness of the given material through which the radiation passes in being transmitted from the source to the detector.

Figure 4:
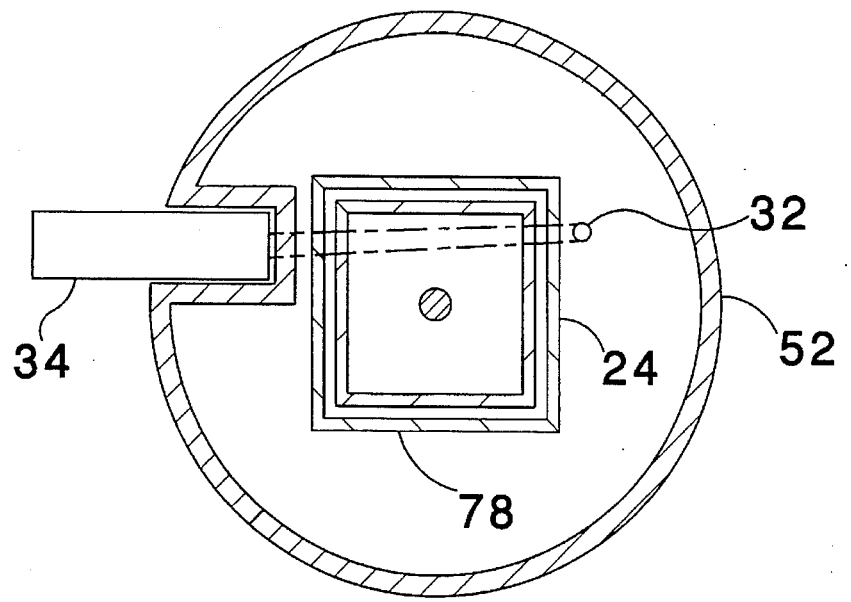
FIG. 4 is a simplified, plan view illustrating the materials between a radioactive source and a detector seen in FIGS. 2 and 3.

Cesium-137 and cobalt-60 are preferred isotopes, employed as radioactive source materials in gauging the level of molten metal and other radiation gauging systems. As is evident from FIGS. 4 and 5, there are a plurality of layers of material between the source 32 and detector 34, sequentially being a layer of water, the flow tube 78 (steel), a layer of water, two walls of the mold tube 24 (copper), a layer of water, the flow tube 78 (steel), a further layer of water and the end wall of the closed tube 90.

In conventional level gauging in a continuous casting process, the several tube walls and water layers are radiation absorbing constants. This is to say that the strength of the radioactive source must be sufficient for the detector to provide a reliable, base output signal. With a sufficiently high base signal, i.e., when there is no metal in the tube 24 that would absorb the radiation being transmitted from the source 32, it is then possible to gauge the level of molten metal in the tube 24. Thus, when the level of metal in the tube 24 rises above point 92, there will be a progressively increasing absorption of radiation up to the point where the level of metal reaches point 94, whereat all of the radiation reaching the detector 34 must pass through molten metal.

With the base radiation level at a sufficiently high level, the decrease in radiation detected by the detector 34, due to a rise in the level of molten metal in the tube 24, can provide a signal output that accurately reflects the level of the molten metal. This signal output is employed for control purposes above described.

There is yet another factor governing the amount of source material required for a gauging function. This is statistical noise. A detector placed in the path of radiation from a fixed source will respond to N particles in any given length of time. The number of responses to N particles reflects the radiation intensity from the source. However, due to random distribution of particles, the detector will also respond to the square root of N, as a standard deviation. The percent of noise is expressed as:

$$\% \text{ Noise} = \left( \frac{\sqrt{N}}{N} \right) \times 100$$

Where there is a large % noise, i.e., when there is a low intensity of the radioactivity detected by the detector, there is an inherent inaccuracy of the output signal being proportional to the amount of radiation that has been absorbed by the medium intervening between the detector and the radioactive source. Thus, in the present case, the strength of the radioactive source 32 must first be in excess of the radiation that will be absorbed by the fixed absorbers (the walls of tubes 24, 32, etc.). The radiation source must also be in excess of what will be absorbed by the molten metal when it fully blocks the radiation field, at point 94, whereat there will be a minimum radiation intensity sensed by the detector 34.

In order for this minimum signal, of minimum strength, to accurately reflect the upper level of the metal, it is necessary that the strength of the source 32 be sufficient for the % noise to be at a low level. It is preferred to maintain the % noise below 1%.

The fixed absorbers and the need for maintaining a minimal % noise factor all contribute to requiring sources of relatively high strength.

To give a further perspective to the problems of level gauging in the environment of continuous metal casting the following relationships of cesium-137 and cobalt-60 and steel, copper and water are provided.

Typical values of μ for cesium-137 and cobalt-60 are given in the following table:

|  | VALUES OF μ | |
|---|---|---|
|  | Cs-137 | Co-60 |
| Steel | 1.4 | 1.1 |
| Copper | 1.6 | 1.25 |
| Water | 0.2 | 0.16 |

The formula for the reduction factor r, as given above is for a situation where there is a single object disposed between the source and the detector. Where, as is the case in gauging the level of molten metal in a continuous casting process, the combined reduction factor is a function of the multiple objects (layers of material) between the source and the material. It is also to be recognized that, where there are multiple objects between the source and detector, the objects nearer the source are deemed to be narrow beam absorbers and have a reduction factor greater than objects nearer to the detector side, the latter being referenced as broad beam absorbers.

With the foregoing in mind, the following reduction factors r are provided to give a general idea of the affect of absorbers of various thickness, on the radiation transmitted from a source to detector.

|  |  | Reduction Factor $e^{\mu t}$ | | | |
|---|---|---|---|---|---|
|  | Thickness | ½" | 1" | 1½" | 2" |
| Cs-137 | Steel | 2 | 4 | 8 | 16 |
|  | Copper | 2.2 | 5 | 12 | 25 |
|  | Water | 1.1 | 1.2 | 1.3 | 1.4 |

-continued

| Thickness | Reduction Factor $e^{\mu t}$ | | | |
|---|---|---|---|---|
| | ½" | 1" | 1½" | 2" |
| Co-60  Steel | 1.75 | 2.7 | 4 | 7.5 |
| Copper | 1.9 | 3.5 | 7 | 11 |
| Water | 1.05 | 1.1 | 1.15 | 1.2 |

Taking all the foregoing relationships into account, the basic equation for determining the strength of a radioactive source required for transmission through multiple objects disposed between a source and a detector may be expressed as:

$$S = \frac{d^2}{K_i} \cdot I_o \cdot r_1 \cdot r_2 \ldots \cdot r_x$$

Where S=source strength in millicuries; d=the distance between the source and the detector; $K_i$=a constant, unique to a given isotope(radioactive source) expressed in milli-Roentgens; $I_o$=the theoretical radiation intensity at the detector with only air therebetween; $r_1$=the radiation reduction factor for the first object between the source and detector; $r_2$=the radiation reduction factor for the second object between the source and detector; and $r_n$=the radiation reduction factor for the nth object between the source and detector.

Within the constraints of prior art gauging systems for continuous metal casting, as above discussed, the radioactive source has exceeded a strength that would permit it to be handled without rigorous precautions to prevent its being a health and/or environmental hazard. More specifically, prior art, radioactive sources for this gauging function, were routinely provided in strengths substantial in excess of 10 micro-curies, where cesium-137 was employed and substantially in excess of 1 micro-curie where cobalt-60 was employed.

With this background explanation of the prior art in mind, the improvements of the present invention will be appreciated from the following description of preferred embodiments.

Reference is next made to FIGS. 6–9 for a description of a continuous casting mold 122 wherein the radiation gauging function is provided through the use of radioactive material that is inherently safe and is not subject to governmental regulation.

The basic components of the mold 122 are the same as in the mold 22 previously described. Thus, the mold comprises a vertically disposed mold tube 124. The tube 124 is of circular cross section, as opposed to the square cross section of the tube 24 as shown in the above description of prior art practices. This is simply to point out that the product of continuous casting can be circular in cross section, as well as being square or of other polygonal cross section.

A cooling water, flow defining tube 178 is disposed in concentric relation with the mold tube 124 to define an annular, cooling water flow path therebetween. The mold tube is disposed within a cooling water chamber 150 defined, in part by a cylindrical water jacket 152. Cooling water, thus, in conventionally fashion, flows rapidly upward through the flow path between the tubes 124 and 178 to prevent the molten metal from destroying the structural integrity of the mold tube 124, which, as in a conventional mold, is formed of copper.

Figure 6:
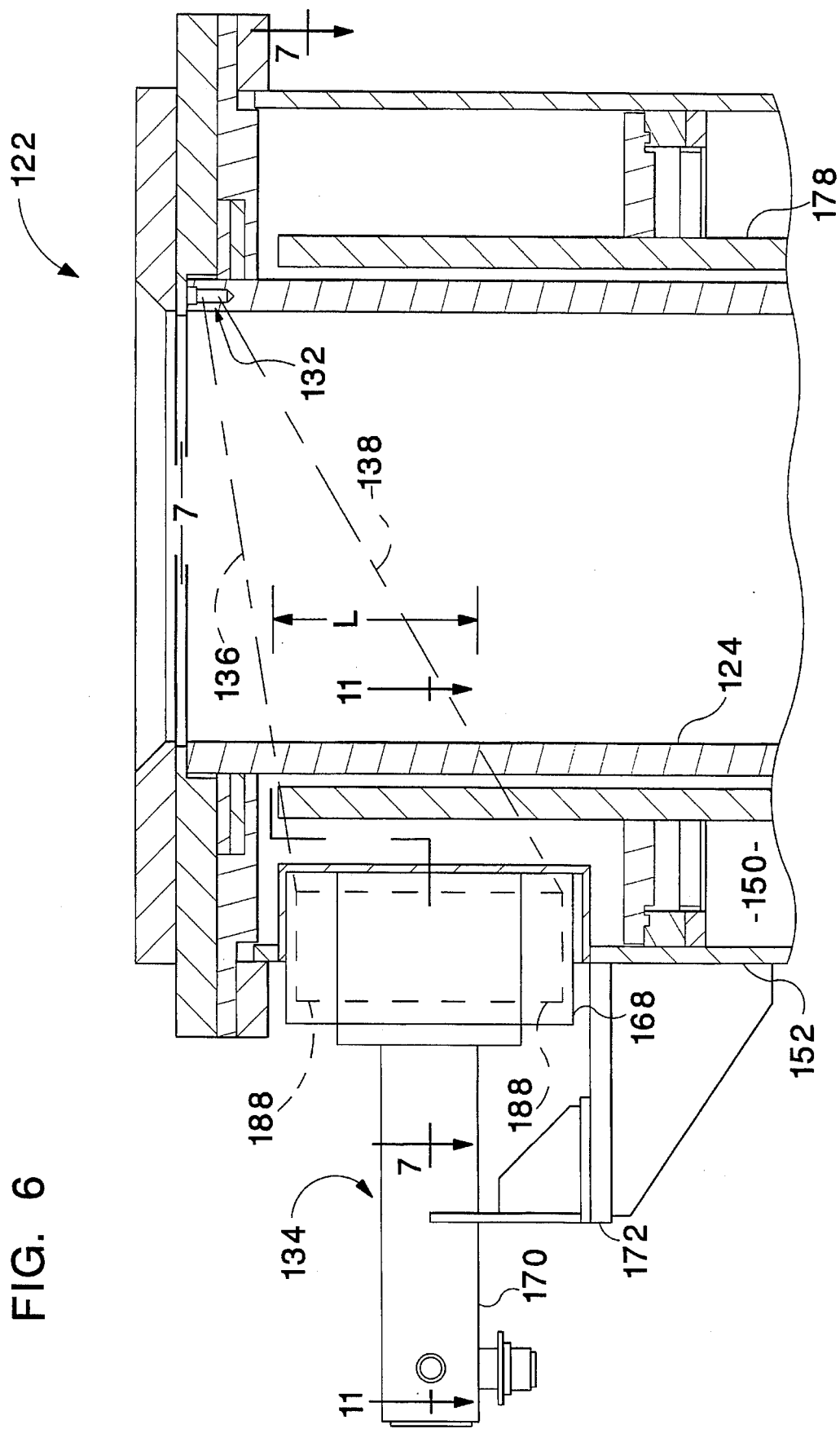
FIG. 6 is a fragmentary elevation, with portions broken away and in section, of the upper end portion of a continuous casting mold, illustrating gauging means of the present invention.
Figure 7:
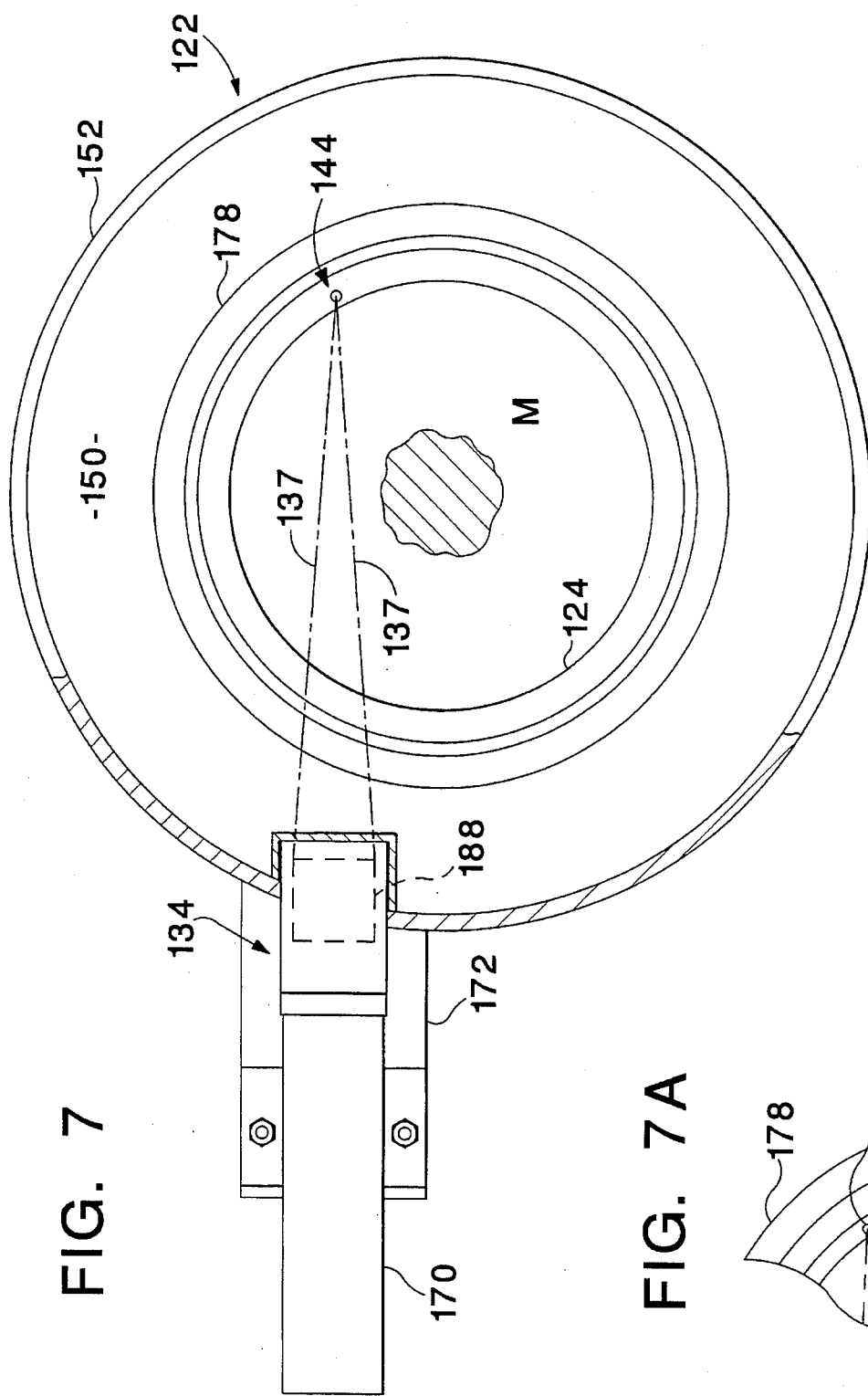
FIG. 7 is a section taken generally on line 7—7 in FIG. 6.

In this embodiment, a "point" radioactive source 132 is employed in combination with a "linear" detector 134. The radiation field is illustrated in FIGS. 6 and 7. The upper and lower bounds of this radiation field are identified lines 136, 138, as seen in FIG. 6. The lateral bounds of the radiation field are indicated by lines 137 in FIG. 7. The range within which the level of molten metal in the tube 124 can be gauged (i.e., the range within which a progressively increasing mass of molten metal will absorb radiation) is indicated by the dimension L.

From FIG. 7 it will also be apparent that the radiation field is laterally offset to the rear of the stream of molten metal M being discharged into the mold tube 122 so that the radiation absorbed by the radiation field will reflect the height of the metal in the mold tube, without factoring in any metal that is in the process in being discharged into the mold tube 122.

Figure 8:
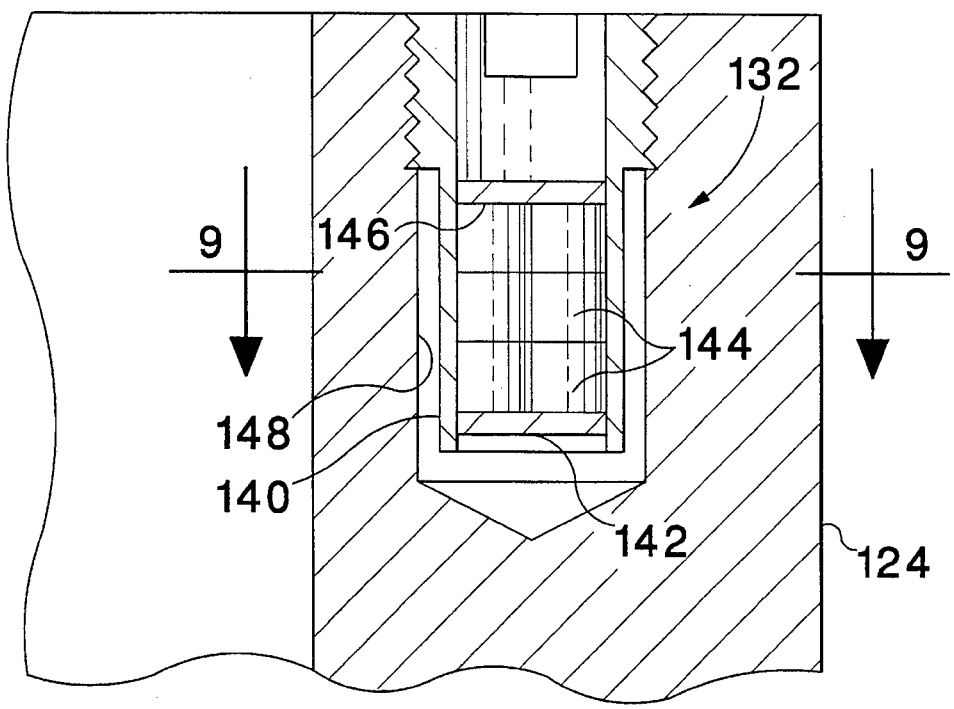
FIG. 8 is a view, on an enlarged scale, of an upper corner portion of a mold tube seen in FIG. 6, illustrating the "point" radioactive source of this embodiment.
Figure 9:
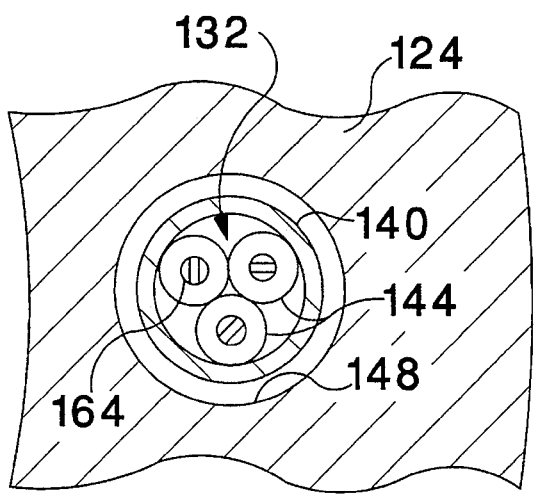
FIG. 9 is a section taken on line 9—9 in FIG. 8.

The point source 132 is best illustrated in FIGS. 8 and 9, where it will be seen that the source comprises a tubular holder 140, the lower end of the holder is closed off by a disc 142. Three stacks of three radioactive source units 144 are disposed within the holder 140. The source units are maintained in the holder 140 by a disc 146. The source holder 140 is inserted in a socket, or blind hole, 148 that extends longitudinally downwardly from the upper, radial end face of the mold tube 124. The upper end of the source holder 140 is threaded into the hole 148 to position the source 132 in its operative position.

Figure 10:
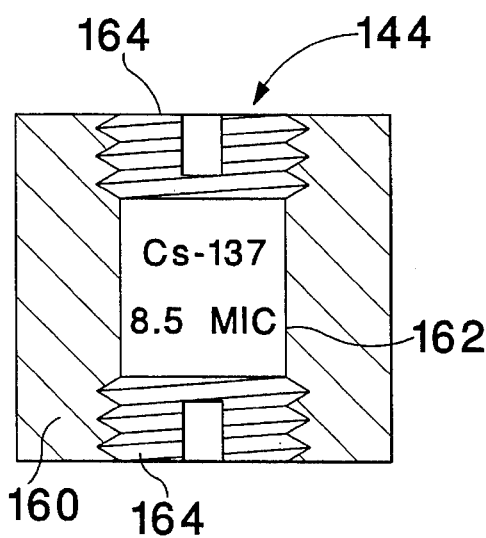
FIG. 10 is an elevation, on a further enlarged scale and partially in section, of a radioactive source unit seen in FIGS. 8 and 9.

The source units 144 (FIG. 10) comprise a tube 160 within which a capsule 162, containing a quantity of radioactive material, is mounted. Screws 164 are threaded into the opposite ends of the tube 160 to maintain the capsule within the tube.

For illustrative purposes, in the embodiment being described, the radioactive material is cesium-137. The amount of cesium in each capsule 162 is 8.5 micro-curies. This is a quantity that qualifies as being inherently safe. Each of the units is marked, as by engraving, with an identification of the radioactive material that is disposed in the capsule 162. There are nine units of this inherently safe quantity so that the aggregate of safe units is also inherently safe.

The length of each radioactive unit 144 is 0.25 inches and its diameter is 0.140 inches. The compactness of the individual radioactive units 144, enables them to be mounted in the wall of the mold tube 124, which, illustratively, has a wall thickness of ¾ inch.

By disposing the source 132 in the end wall of the mold tube 124, the inherent distance between the source 132 and the detector 134 is reduced. Since the strength of the source radiation is a function of the square of the distance between the source and the detector, the reduced distance reduces the required strength for the source.

More importantly, this disposition of the source 132 means that the radiation field must pass through only one wall thickness of the cooling path tube 178, as opposed to the need for the radiation field to pass through two walls of the cooling path tube in prior art configurations. In this fashion there has been a substantial reduction in the environmentally fixed absorbers that contribute to the minimum radiation strength requirements for the source 132.

A further advantage of the described disposition of the source 132 is that it enables the upper range of gauging (distance L) to be closely adjacent the upper end of the mold tube 124. By having the upper end of the gauging range closer to the upper end of the tube it is possible to make better use of the full length of the tube in the chilling process. This is extremely important in that, if the upper level of molten metal is gauged at a lower level, there is a greater likelihood, in the event of some unexpected condition, that the bar drawn from the bottom of the mold will not be properly chilled and the molten metal will escape from the bottom of the mold.

Figure 7A:
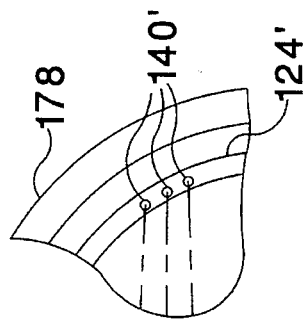
FIG. 7A is a section similar to FIG. 7 illustrating an alternate disposition of radioactive sources.

FIG. 7A illustrates an alternate disposition of radioactive units, where the thickness of a mold tube 124' is insufficient to accommodate a source holder that has a diameter sufficient to hold three stacks of three radioactive units 144. In such case the equivalent radioactive strength can be provided by the provision of three source holders 140' are mounted, in closely spaced relation in recesses formed in the upper, radial end surface of the tube 124. Each of the holders 140' contains a single stack of radioactive units (not shown) which may be the same as the units 144, previously described.

An additional advantage is found in that the source is mounted in a manner that has virtually no impact on the structural integrity of the mold tube. This is to point out that, the level of molten metal is normally maintained at or below the level of the source 132. Thus, there is little or no hydraulic force, from the molten metal, acting on the tube 124 that would induce stresses in the tube. Further, the integrity of the outer surface portion of the tube, which is the most highly stressed portion of the tube, is maintained intact.

Figure 11:
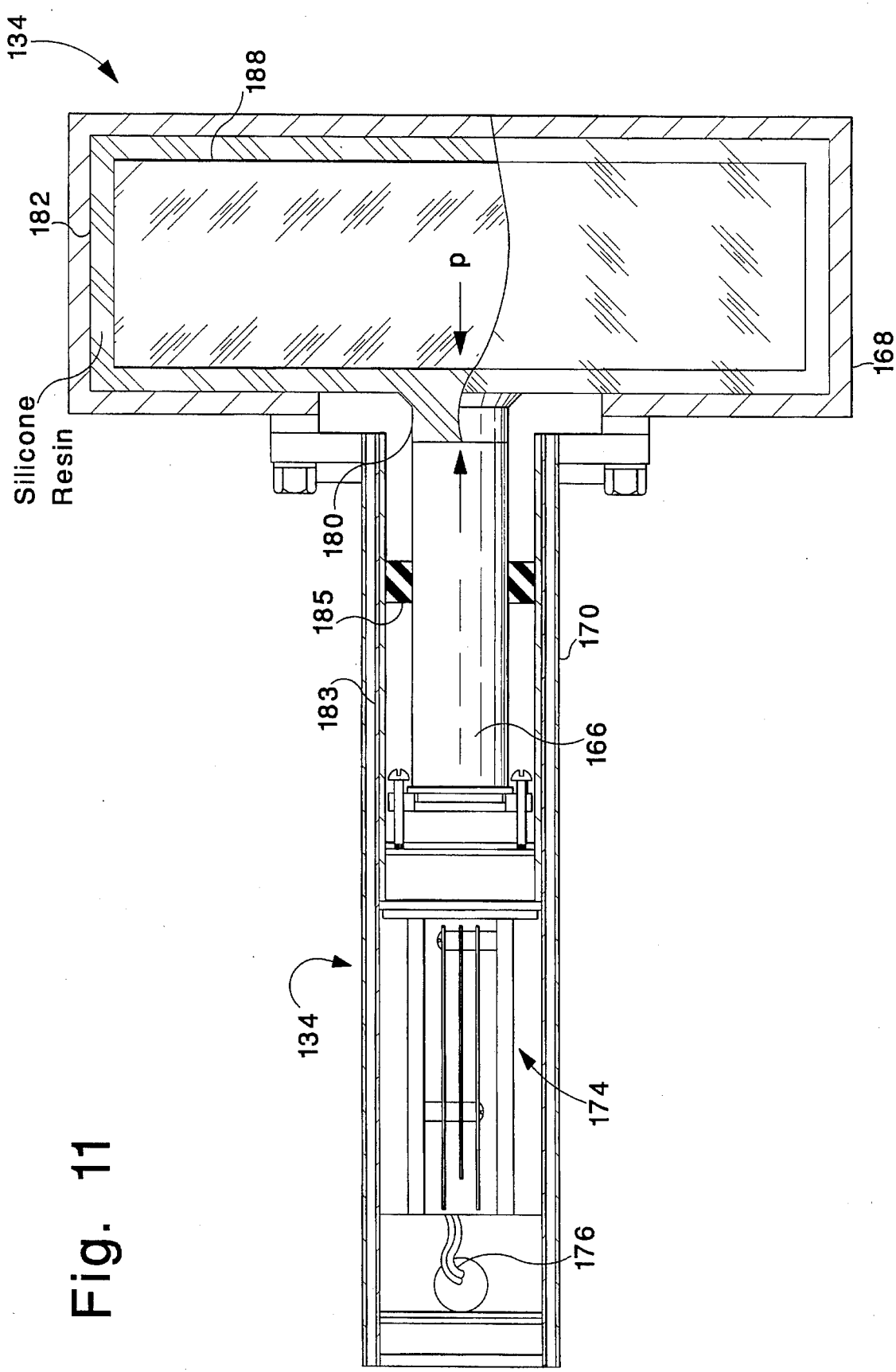
FIG. 11 is a section taken on line 11—11 in FIG. 6, further illustrating the detector employed in this embodiment of the invention.

The ends of the present invention are also attained through the construction of the detector 134, as will now be described, with reference to FIG. 11.

The detector 134 comprises a scintillation crystal 188 and a photomultiplier 166. The crystal 188 is formed of sodium iodide. Sodium iodide crystals are a known and highly effective means for converting gamma ray energy into light energy. Sodium iodide crystals have been previously employed in detectors for gauging systems and molten metal gauging systems in particular. The present invention greatly enhances the effectiveness of scintillation detectors employing such, or equivalent crystals, as will now be further detailed.

The crystal 188 is mounted within a compositely formed housing 168, which for simplification of the disclosure is illustrated as a unitary member. The housing 168 is secured to the forward end of the a tubular housing 170. A bracket 172, projecting from the water jacket housing 152 receives the housing 170 in supporting the detector 134 (FIG. 6).

The detector 134 functions in conventional fashion in that radiation energy, impinging on the crystal 188, is converted into light energy of very short duration. There is a flash of light for each particle of disintegration from the source 132. Again in accordance with known principles, the flashes of light in the crystal are transmitted to the photomultiplier 166, also referenced as a photo-tube. The photo-tube functions to produce electrical pulses which are then processed by circuitry, indicated at 174 to provide an output signal, by way of conductor 176, that indicates the level of molten metal in the tube 124.

The described process of converting radiation energy to light energy in the crystal and then converting light energy to electric pulses in the photomultiplier is well known, as is the further step of converting the electric pulses into an output signal that reflects the height of molten metal in the tube 124.

The sensitivity of the detector is a function of several parameters. The first factor is the percent of the radiation field, emitted from the source, that impinges on the crystal of the detector. This is primarily a function of the surface area of the crystal that is disposed normal to the direction of radiation emission. It is also known that the sensitivity of a detector increases as the thickness of the crystal increases (that is its dimension in the direction of radiation emission).

It is to be recognized that an increase in the sensitivity of a detector decreases the strength of radiation required at the source. As indicated above, it has been previously recognized that increases in detector sensitivity can be achieved by increasing the size of the detector's crystal. However, prior detectors for the rugged environment of gauging the level of molten metal, have failed to realize the advantages of larger crystals, to large extent because of the additional environmental factor of vibration.

The reason for this failure is that photomultiplier tubes have a relatively delicate, fragile phototube, glass surface to which the crystal must be connected. In conventional detectors, the phototube and the crystal have approximately the same dimensions (typically 1 inch diameters) and the crystal is coupled directly to the phototube by a thin film of silicone grease. This connection does meet the basic requirement of a highly efficient transmission of light flashes from the crystal to the photomultiplier tube.

Any substantial increase in the mass of the crystal, particularly when disproportionate to the diameter of the phototube, puts the fragile, phototube in jeopardy due to the high vibrations experienced in the continuous casting process. Put another way, because of the vibrational environment, it has been accepted that the detector crystals must be generally limited to cylindrical crystals having a length approximating their diameters. It has thus been a practice to employ detectors of limited sensitivity, notwithstanding that it is well know that increased sensitivity (and decreased strength requirements for the radioactive source) can be attained by increases the lateral extent of a crystal and/or its thickness.

The present invention enables the use of detection crystals of increased size and therefore increased efficiency, to the end the strength requirements for the source 132 can be maintained at low levels. This end is attained through the provision of a resinous, "lightpipe" connection 180 between the crystal 188 and the phototube 166. The "lightpipe" connection 180 is integral with and formed of the same material as a casing 182 in which the crystal 188 is enclosed. The casing 182 is disposed and substantially fills the spacing between the crystal 188 and the housing 168.

The resinous material found best suited for the "lightpipe" connection 180 and the casing 182 is a catalyst/air cured polysilicone resin a high optical clarity. Such resins are commercially available and generically known as optical interface compounds. One suitable compound is available from Rexon Components, Inc. (Willoughby, Ohio), under the identification "RX-22P". Dow Corning, Inc. also produces a suitable resin under the trade identification Sylguard.

It is known to use such optical interface compounds to provide an interface connection between a gamma camera plate and a phototube. The present invention extends those teaching to provide a scintillation detector of greatly enhanced sensitivity as well as enabling its use in the harsh operating environment of a continuous casting mold.

To this end, it has been found that, based on a phototube diameter of 1⅛ inch, an effective length p for the "lightpipe" connection 180 is approximately 0.650 inch. Further, it is preferred that the "lightpipe" connection 180 be flared outward at its juncture with the casing 182, is indicated. A flare angle of 45° to a diameter of about 1.40 inches has been found effective.

The latter end of enabling use in a harsh environment is attained through the shock absorbing capability of the resinous compound that forms both the connection 1880 and the casing 182. The resinous material has a highly resilient characteristic, while being relatively soft, in the range of a Shore durometer of 45. These characteristics are maintained over a wide range of operating temperatures and are virtually immune to change over an extended operating life.

The phototube 166 is mounted in fixed relation to a tube 183 disposed internally of the tube 170. A resilient, shock absorbing 185 positions the phototube 166 centrally of the tube 183 and in fixed relation to the crystal 188, as it is mounted in the housing 168. Thus, even though the crystal 188 has a size and mass substantially greater than the phototube 166, the cushioning effect of the "lightpipe" connection 180 and the casing 182 isolates one from the other so that there is little of no transmission of vibration loadings between the phototube and the crystal during operation of the continuous casting process.

The "lightpipe" connection 180, has been found highly effective in enhancing the sensitivity of the detector. First, it is an inherent characteristic of the optical interface compound that it has an index of refraction that closely matches the index of refraction of the phototube 166. The material itself thus minimizes any losses in the transmission of light energy therethrough.

The configuration of the "lightpipe" connection 180 is also significant, particularly its length dimension p. It has been found that the sensitivity of the detector decreases if the p dimension varies to any substantial extent, when used with a crystal and phototube of the dimensions given. Put another way, the sensitivity of the detector is increased compared to the conventional practice of "closely coupling" a crystal and phototube, through the use of a thin film of silicone grease, or optical interface compound.

The increase in sensitivity due to the use of a lightpipe of substantial length, is deemed to be due to a reduction of "noise". This is to point out that radioactivity exists within the phototube 166. This radioactivity can radiate back into the crystal, causing a light flash that is then converted to an electrical pulse by the phototube and falsely read as an emission from the source 132. The increased length (compared to a "close coupling") of the "lightpipe" connection 180 minimizes light flashes in the crystal 188 due to radiation emanating from the phototube 166.

Sensitivity is also enhanced by reason of the fact that there is a reduced differential between the intensity of light flashes generated in the crystal 188, as they are transmitted into the phototube 166. This is significant where the dimensions of the crystal are substantially greater than the diameter of the phototube. This is to point out that a flash can be generated, randomly, anywhere within the confines of the crystal. A flash generated at the lower, front end portion of crystal 188, has a much greater distance to travel than a flash that is generated on the left face of the in the axis of the phototube 166. The fact that both flashes have the additional distance p to travel, reduces the percentage differential between the distance each must travel, as opposed to the differential that would exist in a "closely coupled" crystal.

It is also to be appreciated that the shock absorbing function of the casing 182 is provided without impairing the reflective characteristic of the housing 168. This is to point out that, conventionally, the interior of a housing, in which a crystal is mounted, is formed with a highly reflective surface. When a flash of light is generated in the crystal, light emanates in all directions, the light impinging on the interior of the housing is reflected back through the crystal to provide a stronger light energy signal that will have a greater certainty of being converted into an electrical pulse. The optical interface compound has virtually no impact on the ability of the housing walls to reflect and enhance the strength of light energy flashes. It is to be further understood that the silicone material adheres to the surfaces of both the crystal and the inner surfaces of the housing 168 thereby protecting both surfaces from degradation that would adversely affect this reflective capability.

The described detector, employing a sodium iodide crystal having a height of 6 inches and a width and depth of 2 inches provides an increase in sensitivity in the order of 200:1 as compared to the convention use of a crystal having a diameter of approximately 1 ⅛ inch and a length of approximately one inch. This enables the use of "inherently safe" quantities of cesium-137 in the radioactive units 144 in gauging the level of molten metal in a tube 124 having an internal diameter of 11.25 inches.

Reference is next made to FIGS. 12–15 for a description of another embodiment of the present invention.

The structure of this embodiment is similar to that of the prior art structure of FIGS. 2 and 3. The mold 222 comprises a radioactive source 232 disposed on one side of a mold tube 224 and a detector 234 disposed on the other side of the mold tube. The mold tube 224 is disposed in a water jacket comprising an outer cylinder 252, with the source 232 being disposed in the water chamber 250 and the detector projecting into the water bath by way of a closed tube 290. A tube 278 defines a cooling water flow path in combination with the tube 224.

The linear radioactive source 232 differs from the conventional source 32 in that it comprises radioactive source units that are deemed "inherently safe".

The radioactive source comprises (FIGS. 14, 15) a plurality of radioactive units 244, that may be of the same construction as the units 144, previously described. The units 244 are mounted in spaced relation along the length of a tube 245. The units 244 are, each mounted within a sleeve 247. The units are spaced apart by spacers 249 that have a diameter and length approximating the diameter and length of the sleeves 247. It is thus possible to interchange spacers and sleeve/radioactive units and concentrate the radioactive at any point along the height of the tube 245.

There may be a total of up to ten radioactive units 244. In the present illustrative embodiment, the radioactive units each comprise cesium-137 with a strength of 8.5 microcuries.

The detector 234 differs from the detector 34 in that it is linear in its detection characteristics. The use of linear detectors in combination with a linear radioactive source, is a known technique for increasing the sensitivity/efficiency of a gauging system for measuring the level of a liquid over an extended range. However, the accepted practice in the continuous casting art has been to employ "point" detectors. By doing so, the distance between the detector and a radioactive source can be substantially reduced by disposing the detector interiorly of the water jacket, by disposing it in a the closed tube. However, in mounting the detector directly on the water jacket and with the detector projecting into the water jacket, the high vibrations existing during the casting process have led to the accepted practice of employing a "point" detector, with a relatively small diameter and length. All of which has contributed to the accepted practice of employing radioactive source materials in excess of what could be deemed "inherently safe" and free of governmental regulation.

Figure 12:
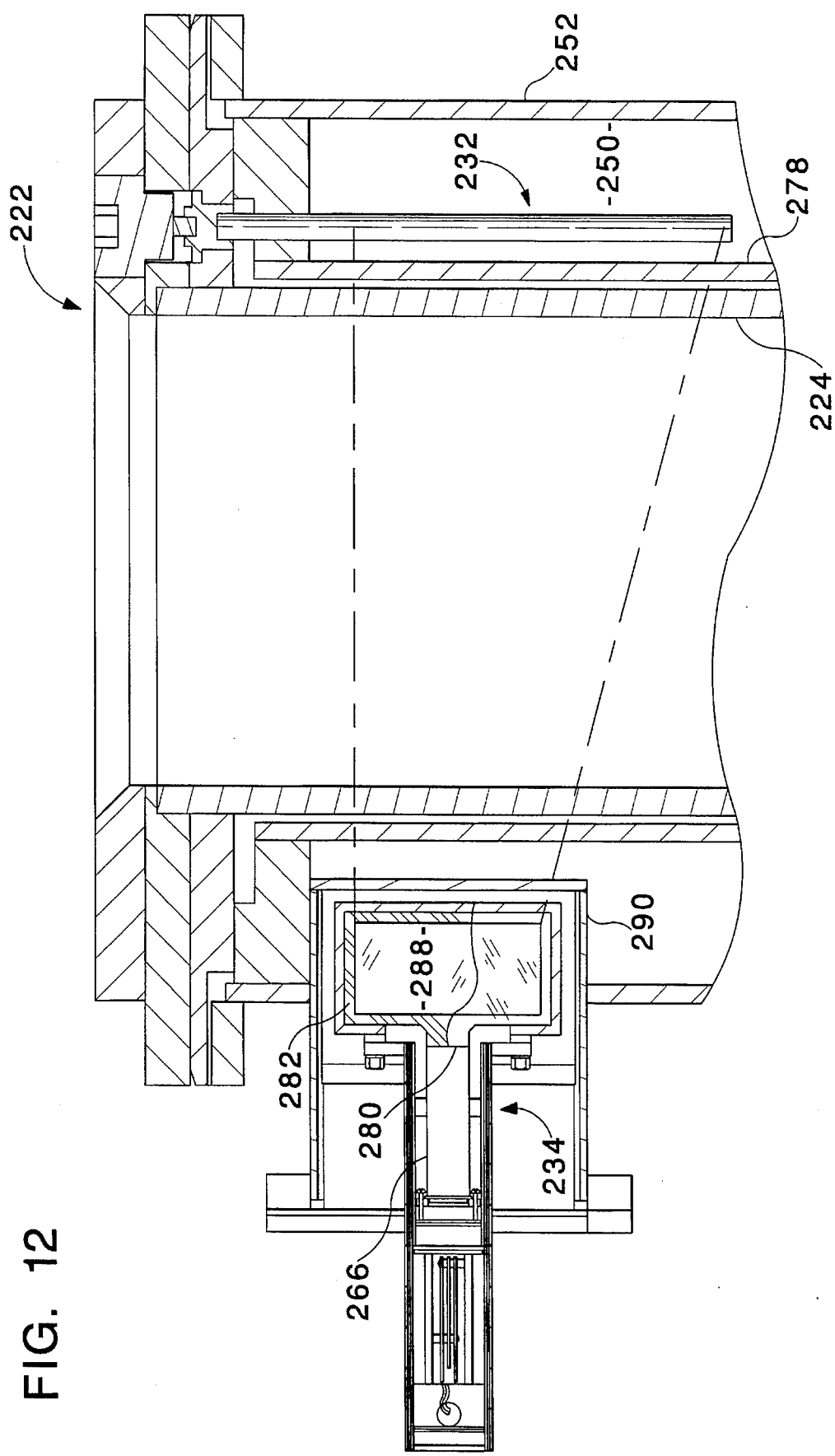
FIG. 12 is a fragmentary elevation, with portions broken away and in section, of the upper end portion of a continuous casting mold, illustrating another gauging means that embodies the present invention.
Figure 13:
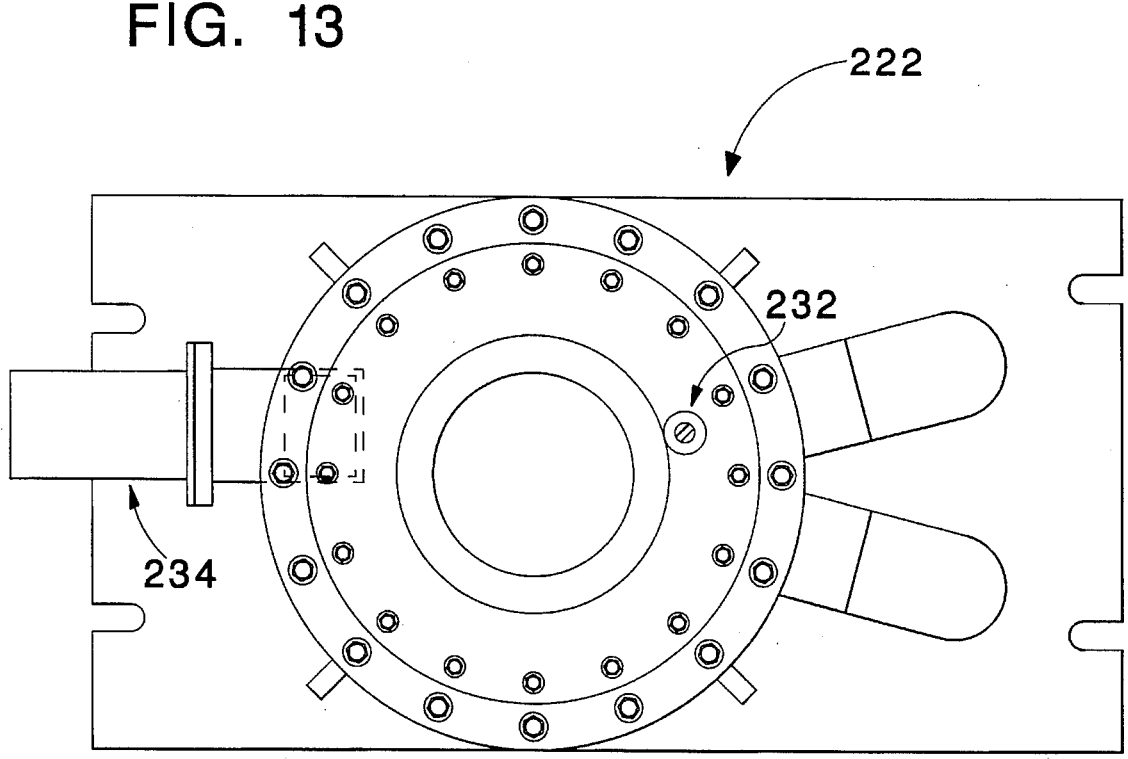
FIG. 13 is a plan view, on a reduced scale, of the mold seen in FIG. 12.
Figure 14:
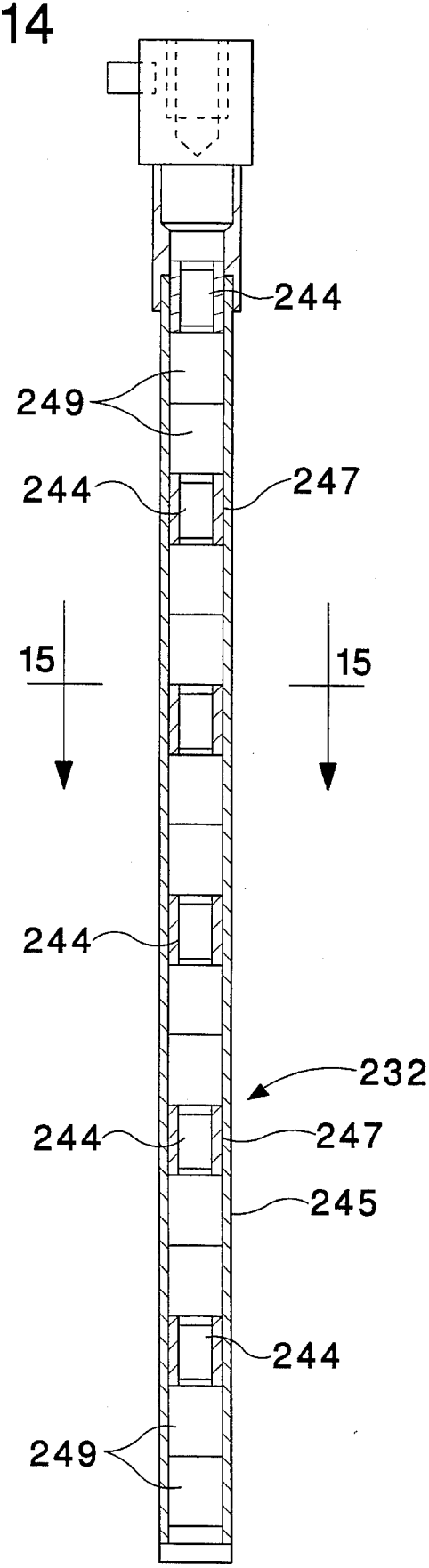
FIG. 14 is an elevation, on an enlarged scale, of a linear source seen in FIG. 12.
Figure 15:
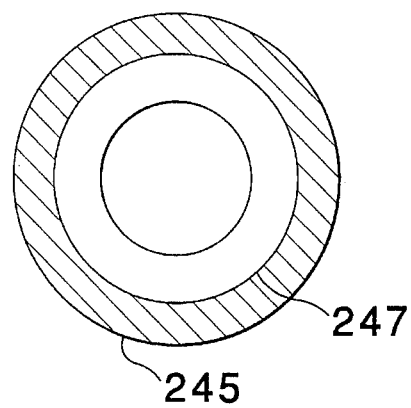
FIG. 15 is a section, on a further enlarged scale, taken on line 15—15 in FIG. 14.
Figure 16:
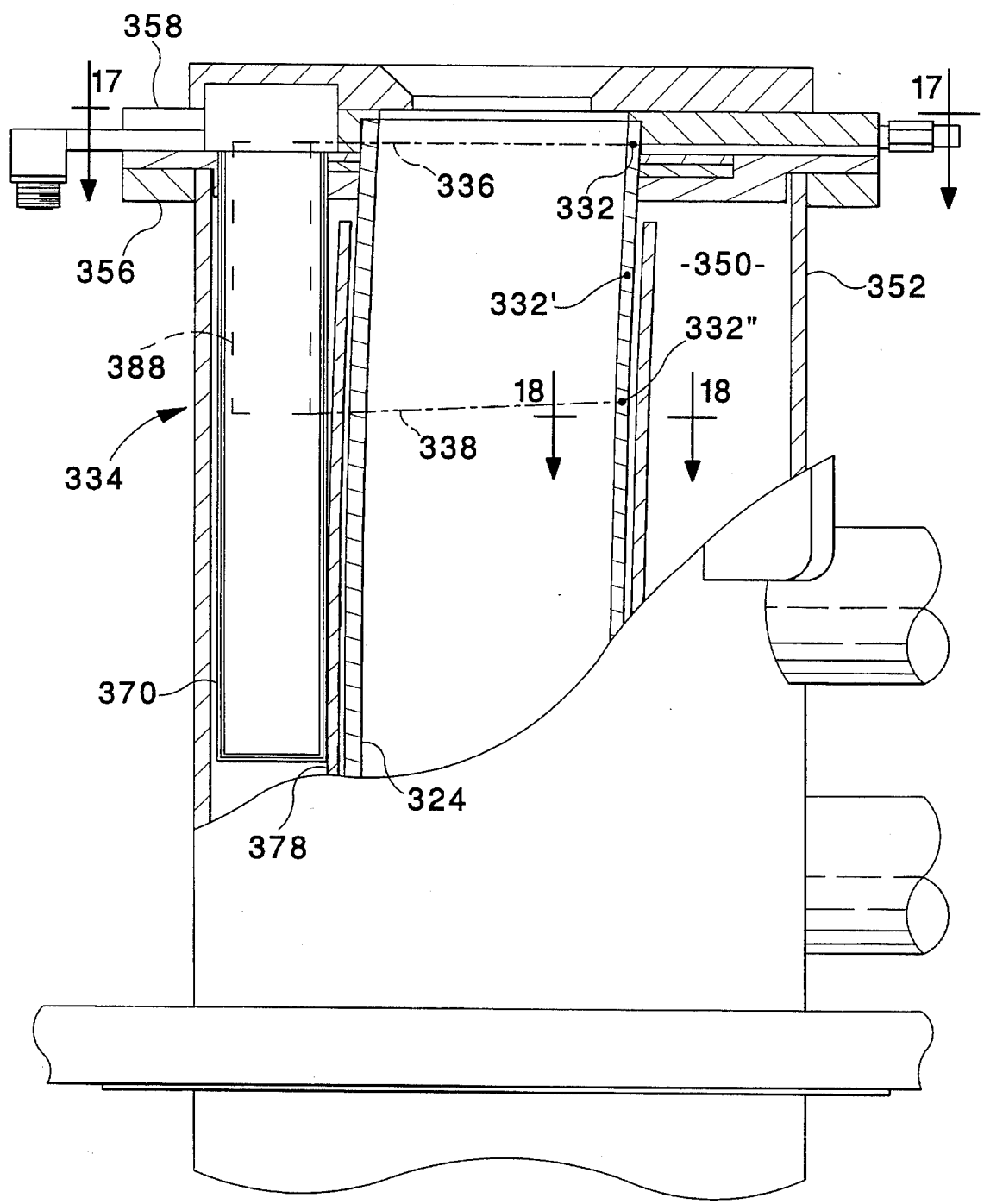
FIG. 16 is a fragmentary elevation, with portions broken away and in section, of the upper end portion of a continuous casting mold, illustrating yet another gauging means that embodies the present invention.
Figure 17:
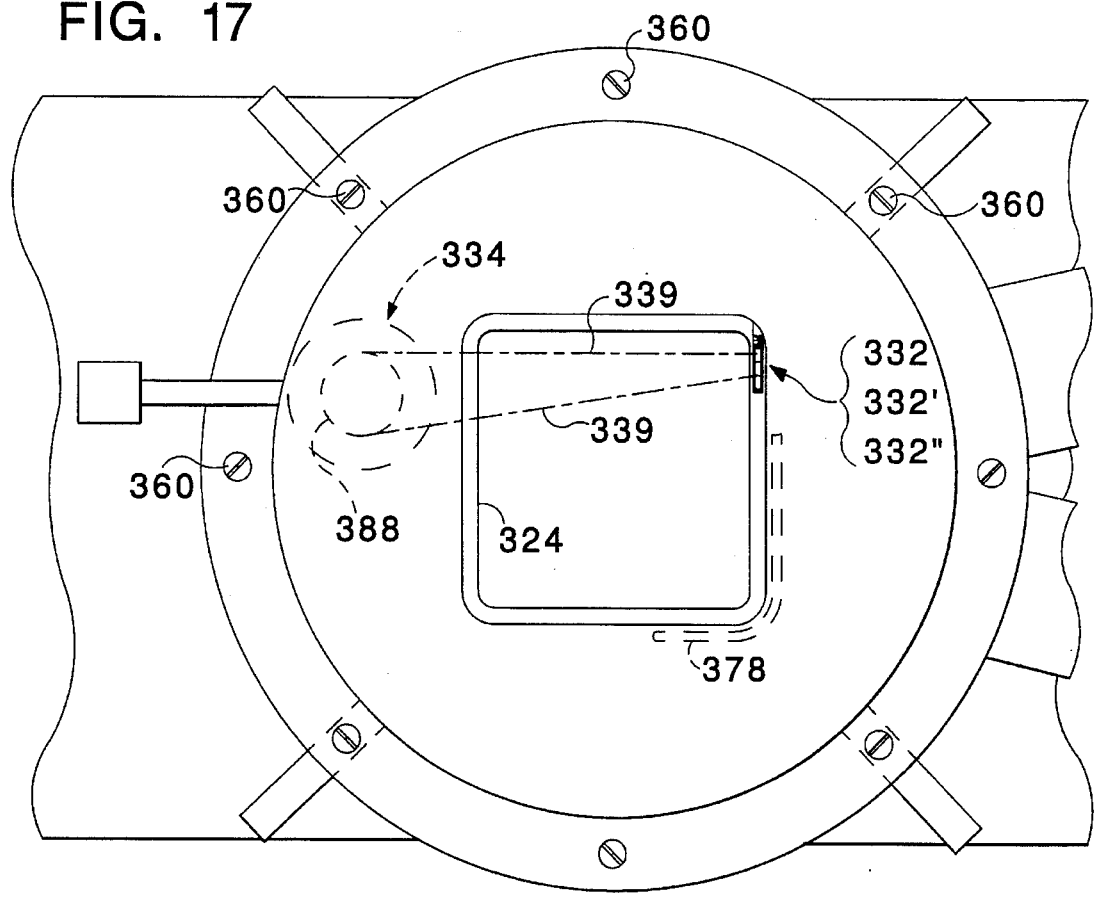
FIG. 17 is a section taken generally on line 17—17 in FIG. 16.
Figure 18:
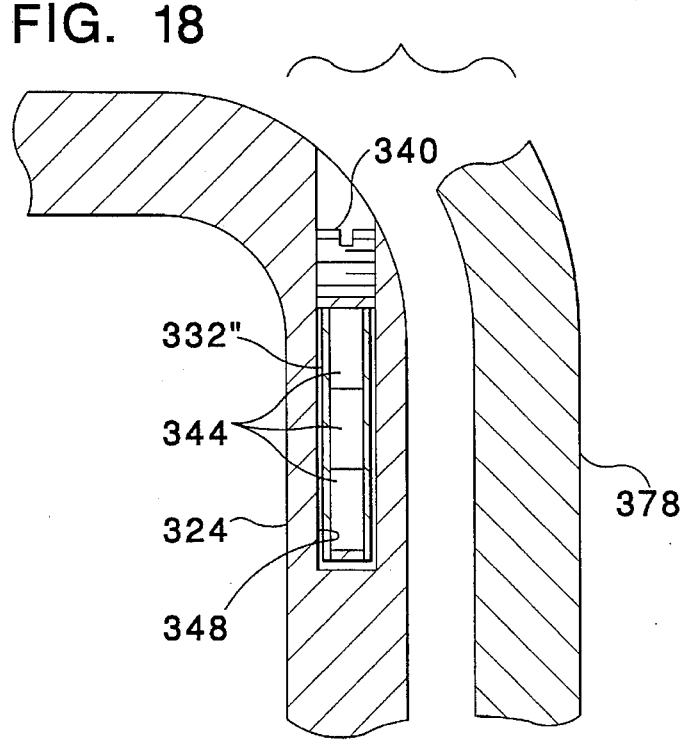
FIG. 18 is a section, on an enlarged scale, taken on line 18—18 in FIG. 16, illustrating a radioactive source.
Figure 19:
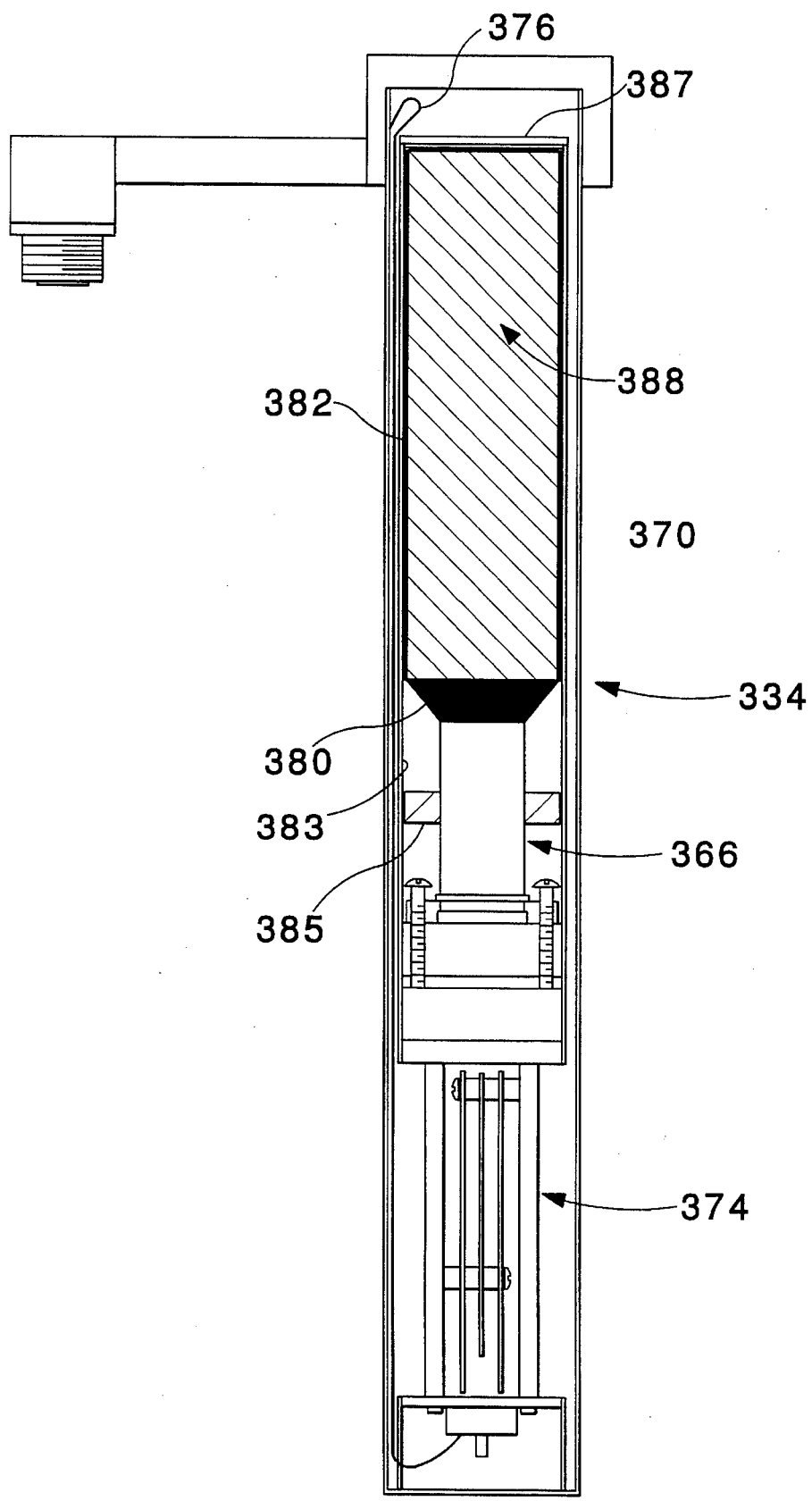
FIG. 19 is an elevation illustrating, in greater detail, the detector seen in FIG. 16.

The detector construction, illustrated in FIG. 12, illustrates the use of an optical interface compound lightpipe 280 connecting a scintillating crystal 288 and a photomultiplier 266 and a casing 282, formed of the same material, which mounts the crystal in a housing 268. The lightpipe 280 and casing 282 provide the same advantages of shock absorption and efficient light transmission described in connection with the previous embodiment. Thus it is possible to accommodate the relatively large scintillation crystal 288 and achieve the higher efficiencies of employing a line detector and line radioactive source in a closely spaced relation, all of which reduces the required strength of the radioactive source units 244.

Reference is next made FIGS. 16–19 for a description of yet another embodiment of the invention.

This embodiment is, likewise, illustrated in the environment of a continuous casting process, wherein it is desired to gauge the level of molten metal in a mold tube 324. The tube 324 is disposed within a water jacket comprising an outer cylindrical tube 352. As before there is a cooling water, flow path defining tube 378 closely spaced from the mold tube 324 so that there will be a rapid flow of cooling water that will enhance the heat transfer rate to prevent overtemperaturing of the mold tube.

In this embodiment three radioactive sources 332, 332' and 332" are employed in generating a vertically linear radiation field that impinges on a vertically linear detector 334 comprising a scintillation crystal 388. The upper and lower bounds of this radiation field are defined by lines 336, 338. The lateral bounds of the radiation field are identified by lines 339 in FIG. 17.

Each of the sources 332, 332' and 332" comprises a source holder 340 that is inserted into a horizontal, blind hole 348 that extends inwardly from a corner portion of the square tube 324. The holders 340 are threadably engaged in the holes, or recesses, 348 to position radioactive source units 344 so that the radiation therefrom needs to pass through only a small portion of the thickness of the tube 324 in passing to the detector 334.

The detector comprises an outer, tubular housing 370, which projects downwardly from a mold tube mounting plate 358, which is appropriately sealed to a water jacket flange 356, being secured thereto by screws 360. The detector is thus disposed directly in the water chamber 350, minimizing the mass of fixed absorbers between it and the sources in holders 340, as well as further minimizing the distance therebetween.

It is to be further noted that the upper portion of the radiation field, on both the detector side and the source side, is now disposed above the flow defining tube 378 and very closely approaches the top of the mold tube 324. The importance of being able to monitor the level of molten level closely adjacent the upper end of the mold tube has been previously discussed. This configuration, wherein the detector is mounted on and projects downwardly from a plate that defines the upper end of the mold cooling, water jacket, further enhances the ability to monitor molten metal levels closely adjacent the upper end of the mold tube.

It is also to be noted that the mounting plate 358 is readily removable from the flange 356. When the plate 358 is removed, the detector 358 is removed with it. Thus there is no impediment to access to the interior of the water jacket, for maintenance or repair functions.

The construction of the detector 334 is similar to that of the detectors 134 and 234, previously described. Thus the detector comprises the crystal 388, disposed at the upper end of the tube 370. The crystal, again, is a sodium iodide crystal. In this embodiment the crystal has a circular cross section. The crystal 380 is provided with an optical interface compound lightpipe 380 connecting the scintillating crystal 388 and a photomultiplier 366. The photomultiplier tube is mounted by a shock absorbing ring 385 in fixed relation to an interior tube 383. The scintillation crystal is also provided with a shock absorbing casing 382 that fills the space between the crystal and the interior tube 383, as well as the space between the upper end of the crystal and an and cap 387 for the tube 383. The casing 382, as before, can be formed of the optical coupling compound and integrally with the lightpipe 380. The shock mounting and light transmission advantages, previously described, are thus provided for in this embodiment. It is to be noted that the mass of the crystal 388 is likewise substantially greater than the prior practices previously discussed, note that its diameter is approximately 50% greater than that of the mating end of the photomultiplier tube 366, and its length is approximately four times its diameter.

The detector 334 further comprises electronic circuitry 374 that process the electrical signals, generated in the photomultiplier tube 366, into an appropriate output signal that is fed to an appropriate controlling means through a conductor 376.

The described radiation gauging means of this embodiment likewise enable the gauging function to be performed employing radiation units that have a strength that is deemed "inherently safe"

Variations from the embodiments herein described will occur to those skilled in the art, within the spirit and scope of the present inventive concepts, and the following claims are to be interpreted and applied with this factor in mind.

Having thus described the invention, what is claimed as novel and desired to be secured by Letters Patent of the United States is:

1. A continuous casting mold comprising
 a generally vertically disposed mold tube into which molten metal is discharged,
 means defining a water jacket surrounding said mold tube and including a flow defining tube closely spaced from said mold tube and defining, in combination therewith a restricted cooling water flow path through which water passes at a rapid rate to prevent the molten metal from impairing the integrity of the mold tube, and
 means for gauging the level of molten metal in the mold tube, said gauging means comprising
  a radioactive source disposed on one side of the mold tube and
  a detector disposed on the opposite side of the mold tube, wherein at least one of the radioactive source and the detector is vertically linear,
 characterized in that
  the radioactive source is disposed in a recess in the wall of the mold tube,
  whereby radioactive emissions transmitted to the detector must pass through full thickness of only one wall of the flow defining tube in passing to the detector, whereby the fixed radiation absorption of the mold is minimized to thereby reduce the strength required for the source in gauging the level of molten metal.

2. A continuous casting mold as in claim 1, further characterized in that
 the recess, in which the radioactive source is disposed, extends downwardly from an upper, transverse end face of the mold tube.

3. A continuous casting mold as in claim 1, wherein
 the mold tube has a generally rectangular cross section and
further characterized in that
 the recess, in which the radioactive source is disposed, extends laterally from a corner of the tube into a side wall thereof.

4. A continuous casting mold as in claim 1, further characterized in that the radioactive source comprises
    a capsule containing radioactive material,
    a holder for the capsule, and
    means for removably mounting the holder in said recess.

5. A continuous casting mold as in claim 1, further characterized in that
    the radioactive source is "linear" and comprises a plurality of quantities of radioactive material mounted in the wall of the mold tube and spaced apart in a heightwise sense.

6. A continuous casting mold as in claim 1, further characterized in that
    the radioactive source comprises
        no more than ten radioactive source units and
        each source unit contains a quantity of radioactive material that is inherently safe.

7. A continuous casting mold as in claim 6, further characterized in that
    the radioactive material is selected from the group consisting of cesium-137 in a quantity not exceeding 10 microcuries and cobalt-60 in a quantity not exceeding 1 microcurie.

8. A continuous casting mold as in claim 1,
whereto the mold tube projects above the flow defining tube, and
further characterized in that
    at least a portion of the radioactive source is disposed above the flow defining tube and
    at least a portion of the detector is disposed above the flow defining tube,
    whereby the flow defining tube is not a fixed absorber for an upper portion of the radiation detected by the detector in gauging the level of molten metal in the uppermost portion of the mold tube.

9. A continuous casting mold as in claim 1
wherein
the detector comprises
    a scintillation crystal on which the source radiation impinges, said crystal having the property of converting energy emissions from the source, that impinge thereon, into light energy flashes of short duration, and
    a photomultiplier tube for converting the light energy of the flashes into electrical pulses,
further characterized in that
    the crustal is coupled to the photomultiplier by a "gel" that functions as a light pipe for the efficient transmission of light energy to the photomultiplier and also functions as a shock absorber to protect the photomultiplier from damage.

10. A continuous casting mold as in claim 9,
wherein the photomultiplier has an end face of a given diameter through which light energy passes, and
further characterized in that
    the lateral extent of the face of the crystal, which is connected to the photomultiplier, is substantially greater than the lateral extent of said photomultiplier end face,
    thereby providing an increased sensitivity, for the detector, for a given photomultiplier.

11. A continuous casting mold comprising
a generally vertically disposed mold tube into which molten metal is discharged,
means defining a water jacket surrounding said mold tube and including a flow defining tube closely spaced from said mold tube and defining, in combination therewith a restricted cooling water flow path through which water passes at a rapid rate to prevent the molten metal from impairing the integrity of the mold tube, and
means for gauging the level of molten metal in the mold tube, said gauging means comprising
a radioactive source disposed on one side of the mold tube and
a detector disposed on the opposite side of the mold tube, wherein
at least one of the radioactive source and the detector is vertically linear, and
wherein
the detector comprises
    a scintillation crystal on which the source radiation impinges, said crystal having the property of converting energy emissions from the source, that impinge thereon, into light energy flashes of short duration, and
    a photomultiplier tube for converting the light energy of the flashes into electrical pulses,
characterized in that
    the crystal is coupled to the photomultiplier by a "gel" that functions as a light pipe for the efficient transmission of light energy to the photomultiplier and also functions as a shock absorber to protect the photomultiplier from damage.

12. A continuous casting mold as in claim 11, further characterized by
housing means in which the crystal and photomultiplier are mounted, and
a layer of "gel" between the crystal and the housing means to isolate the crystal from vibrations induced into the housing means.

13. A continuous casting mold as in claim 11, wherein
the photomultiplier has an end face of a given diameter through which light energy passes, and
further characterized in that
    the lateral extent of the face of the crystal, which is connected to the photomultiplier, is substantially greater than the lateral extent of said photomultiplier end face,
    thereby providing an increased sensitivity, for the detector, for a given photomultiplier.

14. A continuous casting mold as in claim 11, wherein
the photomultiplier has an end face of a given diameter through which light energy passes, and
further characterized in that
    the crystal has a mass substantially greater than the mass of a crystal having a diameter equal to the diameter of said end face and a length substantially equal to said diameter,
    thereby providing an increased sensitivity, for the detector, for a given photomultiplier.

15. A casting mold comprising
a generally vertically disposed mold tube into which molten metal is discharged,
means defining a water jacket surrounding said mold tube and including a flow defining tube closely spaced from said mold tube and defining, in combination therewith a restricted cooling water flow path through which water passes at a rapid rate to prevent the molten metal for impairing the integrity of the mold tube, and
means for gauging the level of molten metal in the mold tube, said gauging means comprising a radioactive source disposed on one side of the mold tube and a detector disposed on the opposite side of the mold tube, wherein at least one of the radioactive source and the detector is vertically linear, and characterized in that the detector is disposed in the water jacket, thereby minimizing the distance between the source and the detector and also minmizing the quantity of radioactive material required for the gauging function, wherein the water jacket comprises an outer tube, top plate means, and bottom plate means, with the mold tube extending between the top and bottom plate means, further characterized in that the detector is mounted on the top plate means and projects downwardly therefrom between the outer water jacket tube and the mold tube.

16. A casting mold as in claim 15, further characterized in that the detector is mounted on the undersurface of the top plate means, the top plate means, with the detector mounted thereon, is removable from the outer water jacket tube, to facilitate maintenance and replacement of the detector.

17. A casting mold comprising a generally vertically disposed mold tube into which molten metal is discharged, means defining a water jacket surrounding said mold tube and including a flow defining tube closely spaced from said mold tube and defining, in combination therewith a restricted cooling water flow path through which water passes at a rapid rate to prevent the molten metal for impairing the integrity of the mold tube, and means for gauging the level of molten metal in the mold tube, said gauging means comprising a radioactive source disposed on one side of the mold tube and a detector disposed on the opposite side of the mold tube, wherein at least one of the radioactive source and the detector is vertically linear, and characterized in that the detector is disposed in the water jacket, thereby minimizing the distance between the source and the detector and also minimizing the quantity of radioactive material required for the gauging function, further characterized in that the radioactive source is disposed in recess means in the wall of the mold tube, whereby radioactive emissions transmitted to the detector must pass through only one wall of the flow defining tube in passing to there detector, whereby the fixed radiation absorption of the mold is minimized to thereby reduce the strength required for the source in gauging the level of molten metal.

18. A casting mold as in claim 17 wherein the detector comprises a scintillation crystal on which the source radiation impinges, said crystal having the property of converting energy emissions from the source, that impinge thereon, into light energy flashes of short duration, and a photomultiplier tube for converting the light energy of the flashes into electrical pulses, characterized in that the crystal is coupled to the photomultiplier by a "gel" that functions as a light pipe for the efficient transmission of light energy to the photomultiplier and also functions as a shock absorber to protect the photomultiplier from damage.

19. A casting mold as in claim 18 further characterized in that the detector further comprises housing means, the crustal is disposed in an upper end portion of the detector housing and the photomultiplier is disposed therebeneath, and the photomultiplier is disposed in the detector housing in aligned relation therebeneath.

20. A casting mold as in claim 19 wherein the mold tube projects above the flow defining tube, and further characterized in that at least a portion of the radioactive source is disposed above the flow defining tube and at least a portion of the detector crystal is disposed above the flow defining tube, whereby the flow defining tube is not a fixed absorber for an upper portion of the radiation detected by the detector in gauging the level of molten metal in the uppermost portion of the mold tube.

21. A casting mold as in claim 20, further characterized in that the detector is linear in that the crystal has a height dimension substantially in excess of its cross sectional dimension, and the radioactive source is also linear and the recess means for the radioactive source comprise a first recess disposed closely adjacent to the upper end of the mold tube and at least one additional recess, in the wall of the mold tube, spaced therebeneath.

22. A casting mold as in claim 17 wherein the detector comprises a scintillation crystal on which the source radiation impinges, said crystal having the property of converting energy emissions from the source, that impinge thereon, into light energy flashes of short duration, and a photomultiplier tube for converting the light energy of the flashes into electrical pulses, further characterized in that the detector further comprises housing means, the crystal is disposed in an upper end portion of the detector housing and the photomultiplier is disposed therebeneath, and the photomultiplier is disposed in the detector housing in aligned relation therebeneath.

23. A casting mold as in claim 22 wherein the mold tube projects above the flow defining tube, and further characterized in that at least a portion of the radioactive source is disposed above the flow defining tube and at least a portion of the detector crystal is disposed above the flow defining tube, whereby the flow defining tube is not a fixed absorber for an upper portion of the radiation detected by the detector in gauging the level of molten metal in the uppermost portion of the mold tube.

24. A casting mold as in claim 23, further characterized in that the detector is linear in that the crystal has a height dimension substantially in excess of its cross sectional dimension, and the radioactive source is also linear and the recess means for the radioactive source comprise a first recess disposed closely adjacent to the upper end of the mold tube and at least one additional recess, in the wall of the mold tube, spaced therebeneath.

* * * * *